(12) United States Patent
Laurensse (10) Patent No.: US 9,687,407 B2
(45) Date of Patent: Jun. 27, 2017

(54) APPARATUS AND METHOD FOR TREATMENT OF LATERAL EPICONDYLITIS (TENNIS ELBOW)

(71) Applicant: Tennis Elbow R & D Ltd., Edmonton (CA)

(72) Inventor: Mark James Laurensse, Edmonton (CA)

(73) Assignee: Tennis Elbow R & D Ltd., Alberta, CA (US)

( * ) Notice: Subject to any disclaimer, the term of this patent is extended or adjusted under 35 U.S.C. 154(b) by 354 days.

(21) Appl. No.: 14/398,431

(22) PCT Filed: Apr. 30, 2013

(86) PCT No.: PCT/CA2013/000425
§ 371 (c)(1),
(2) Date: Oct. 31, 2014

(87) PCT Pub. No.: WO2013/163733
PCT Pub. Date: Nov. 7, 2013

(65) Prior Publication Data
US 2015/0088045 A1 Mar. 26, 2015

Related U.S. Application Data

(60) Provisional application No. 61/641,149, filed on May 1, 2012.

(51) Int. Cl.
*A61H 1/02* (2006.01)
*A61F 5/04* (2006.01)
(Continued)

(52) U.S. Cl.
CPC ............ *A61H 1/0277* (2013.01); *A61F 5/042* (2013.01); *A61F 5/05858* (2013.01);
(Continued)

(58) Field of Classification Search
CPC .. A61F 5/00; A61F 5/01; A61F 5/0102; A61F 5/0104; A61F 5/0118; A61F 5/013;
(Continued)

(56) References Cited

U.S. PATENT DOCUMENTS

| 4,014,327 A | 3/1977 | Spiro |
| 5,637,078 A | 6/1997 | Varn |

(Continued)

FOREIGN PATENT DOCUMENTS

GB 2385527 A 8/2003

OTHER PUBLICATIONS

International Search Report in related International Application No. PCT/CA2013/000425, mailed Aug. 7, 2013, 5 pages.

*Primary Examiner* — Keri J Nelson
(74) *Attorney, Agent, or Firm* — Cooley LLP (57) ABSTRACT

Apparatuses and methods are provided for the treatment of lateral epicondylitis (tennis elbow) via the stretching of an affected user's restricted muscle(s), be it the extensor digitorum communis (EDC), extensor carpi radialis brevis (ECRB), supinator muscle, or any combination thereof. The apparatus can comprise various adjustable straps and rigid members configured to secure the apparatus to the user's arm and hold the user's interphalangeal joints, metacarpal phalangeal joints, and wrist in flexion, the user's forearm in pronation, and the user's elbow in extension. This combination of joint positions can constitute a desired position which, when held for prolonged periods, can cause the elongation of the restricted muscle tissue. This in turn can cause relief of the user's symptoms of lateral epicondylitis.

20 Claims, 7 Drawing Sheets

(51) Int. Cl.
*A61F 5/042* (2006.01)
*A61F 5/058* (2006.01)
*A61F 5/01* (2006.01)

(52) U.S. Cl.
CPC ...... *A61F 5/05866* (2013.01); *A61F 5/05875* (2013.01); *A61H 1/0285* (2013.01); *A61H 1/0288* (2013.01); *A61F 5/013* (2013.01); *A61F 5/0118* (2013.01); *A61H 2201/165* (2013.01)

(58) Field of Classification Search
CPC .... A61F 5/04; A61F 5/042; A61F 5/05; A61F 5/058; A61F 5/05841; A61F 5/05858; A61F 5/05866; A61F 5/05875; A61H 1/00; A61H 1/02; A61H 1/0274; A61H 1/0277; A61H 1/0285; A61H 1/0288
USPC ................................ 602/20–22; 128/877–881
See application file for complete search history.

(56) References Cited

U.S. PATENT DOCUMENTS

2004/0153016 A1    8/2004  Salmon et al.
2010/0130895 A1*   5/2010  Armstrong ........... A61H 1/0288
                                                601/40

* cited by examiner

APPARATUS AND METHOD FOR TREATMENT OF LATERAL EPICONDYLITIS (TENNIS ELBOW)

RELATED APPLICATIONS

This application claims the benefit, under 35 U.S.C. 0371, as a national stage application of PCT/CA2013/000425, filed Apr. 30, 2013, which claims the benefit of U.S. Provisional Application No. 61/641,149, filed May 1, 2012. Each of the above-identified applications is herein incorporated by reference in its entirety.

TECHNICAL FIELD

The present disclosure is related to the treatment of orthopedic conditions, in particular, apparatuses and methods used to treat lateral epicondylitis, also known as tennis elbow.

BACKGROUND

It is known that lateral epicondylitis (tennis elbow) is an overuse injury occurring in the side of the elbow region of the arm, specifically at the site of the lateral epicondyle. Tennis elbow is a condition where the outer part of the elbow becomes sore and tender. It is commonly associated with playing tennis, though the injury can happen for a variety of reasons.

Muscle imbalances, shortenings and weaknesses have been identified as major biomechanical factors underlying cumulative trauma injuries such as this. There are three primary muscles that are implicated in the pathogenesis of tennis elbow; extensor digitorum communis (EDC), extensor carpi radialis brevis (ECRB), and a portion of the supinator muscle that originates from the lateral epicondyle. These three muscles join to form a single tendon at the lateral epicondyle.

It is theorized that chronic over use of the hands, such as in typing or repetitive gripping or twisting activities can cause inflammation of the muscles resulting in microscopic scarring and shortening of any of the above muscles.

Current apparatuses and methods used do not effectively address the treatment of lateral epicondylitis. While surgeries to lengthen the supinator have been shown to reduce the radial tunnel pressures, surgery is expensive, complicated, and has safety issues associated with it.

It is therefore desirable to provide apparatuses and methods for the treatment of lateral epicondylitis that overcome the shortcomings of the prior art.

SUMMARY

Apparatuses and methods for the treatment of lateral epicondylitis (tennis elbow) are provided. The apparatuses and methods can treat lateral epicondylitis by stretching the EDC, ECRB, supinator muscle, or any combination thereof. A system of straps and rigid members can be used for simultaneously maintaining multiple joints on an affected arm in a position that is desirable for stretching these three muscles. The system of straps can comprise a means for holding the interphalangeal joints of digits two through five of a user's hand in flexed positions, a means for holding a user's metacarpal phalangeal joints of the second through fifth digits in flexion, a means for holding a user's wrist in flexion, a means for holding a user's forearm in pronation and a means for holding a user's elbow in extension. Use of this apparatus and method can allow the tennis elbow muscles to be held in a desirable lengthened position for sustained periods of time. After undergoing multiple courses of treatment, a user's muscles can be lengthened and the associated lateral epicondylitis symptoms can subside.

Clinically, symptomatic individuals can often have shortening of one or more of the muscles that originate from the lateral epicondyle. These apparatuses and methods can assist in the treatment of tennis elbow for individuals who have a muscular restriction to one or more of these muscles (e.g. EDC, ECRB, or the supinator). In some embodiments, the apparatuses and methods can stretch the supinator and can reduce radial tunnel pressure and therefore reduce the tennis elbow symptoms (in this case, radial tunnel syndrome).

It is difficult to provide a prolonged stretch to one's own forearm extensor muscle group. Even when a trained professional does the stretch passively for the patient, the duration of the treatment may not be long enough to provide an adequate stretch. Apparatuses and methods herein can enable an individual with a tennis elbow condition to easily stretch their muscles at home while relaxing.

Sustained stretches, performed over several treatments to these muscle groups, can abate a patient's symptoms significantly or have them resolve completely. The use of the apparatuses and methods herein can provide individuals with taught extensor muscles with the ability to stretch their forearm extensors in the comfort of their own home to help alleviate or resolve their tennis elbow condition. In some embodiments, the apparatuses and methods herein can stretch the extensor muscles of the forearm in attempts to normalize the biomechanics of the lower arm, thereby reducing or completely relieving a patient of a painful elbow.

A purpose of the apparatuses and methods herein is to stretch the extensor muscle group of the forearm. The asymmetry of a shortened extensor digitorum communis muscle, relative to a flexible extensor carpi radialis brevis, can cause increased stress at the muscles common extensor origin. By elongating this extensor digitorum communis muscle the biomechanics of the forearm can be normalized, which can help in the treatment of the tennis elbow. As well, a shortened supinator muscle may overly compress the posterior interosseous nerve. A lengthening effect on the muscle may relieve compression stress on the nerve.

Broadly stated, in some embodiments, an apparatus for is provided for the treatment of lateral epicondylitis (tennis elbow) by stretching one or more muscles on a user's affected arm, the apparatus comprising: means for holding interphalangeal joints on the affected arm in flexed positions; a distal stabilizing strap for securing the apparatus to a wrist portion of the affected arm; a proximal stabilizing strap for securing the apparatus to an upper arm portion of the affected arm; a rigid member separating the distal stabilizing strap from the proximal stabilizing strap for placing the affected arm's elbow into extension; and a third strap configured to be releasably attachable to the distal stabilizing strap and configured to be releasably attachable to the proximal stabilizing strap or proximate the rigid member, the third strap configured to wrap around the means for holding the interphalangeal joints, and to place the wrist, interphalangeal joints, and metacarpal joints into flexion and to place the affected arm's forearm into pronation and the affected arm's elbow into extension.

Broadly stated, in some embodiments, a method is provided for the treatment of lateral epicondylitis (tennis elbow) by stretching one or more muscles on a user's affected arm, the method comprising: holding interphalangeal joints of digits two through five of the affected arm's hand in flexed positions; holding the affected arm's wrist in flexion; holding the affected arm's forearm in pronation; and holding the affected arm's elbow in extension; thereby stretching the one or more muscles and treating the lateral epicondylitis.

Broadly stated, in some embodiments, an apparatus is provided for the treatment of lateral epicondylitis (tennis elbow) by stretching one or more muscles on a user's affected arm, the apparatus comprising: a proximal stabilizing strap for securing the apparatus to an upper arm portion of the affected arm; a rigid member attached to the proximal strap for placing the affected arm's elbow into extension; wherein the distal end of the rigid member is configured to releasably attach to a distal stabilizing strap for securing the apparatus to a wrist portion of the affected arm.

Broadly stated, in some embodiments, an apparatus is provided for the treatment of lateral epicondylitis (tennis elbow) by stretching one or more muscles on a user's affected arm, the apparatus comprising: means for holding interphalangeal joints on the affected arm in flexed positions wherein the means for holding the interphalangeal joints comprises a glove to hold the interphalangeal joints of the digits of the user's hand in flexed positions, the glove comprising two flat bars attached across the fingers of the glove, the flat bars configured for squeezing the interphalangeal joints into flexion when the flat bars are brought towards each other; and wrap-around glove straps configured to hold the interphalangeal joints in flexion after the flat bars are brought towards each other.

DETAILED DESCRIPTION OF EMBODIMENTS

Apparatuses and methods are provided for the treatment of lateral epicondylitis (tennis elbow) via the stretching of a user's muscles on an affected arm that can contribute to tennis elbow, for example EDC, ECRB, supinator muscle, or any combination thereof. In particular, an apparatus and method for the treatment of lateral epicondylitis is provided that can use a system of straps and rigid stays to simultaneously hold the interphalangeal joints of digits two through five of the user's hand in flexed positions, the user's wrist in flexion, the user's forearm in pronation and the user's elbow in extension. Repeated use of the apparatus and method can be performed over multiple courses of treatment until the user's lateral epicondylitis symptoms have subsided.

Figure 1:
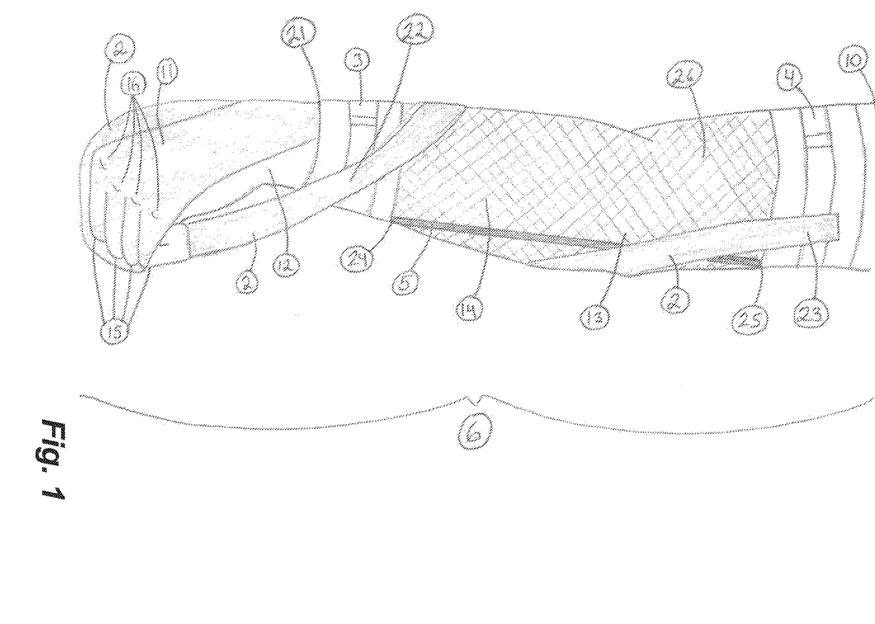
FIG. 1 is a side elevation view of an embodiment of an apparatus as used on a user's affected arm.
Figure 2:
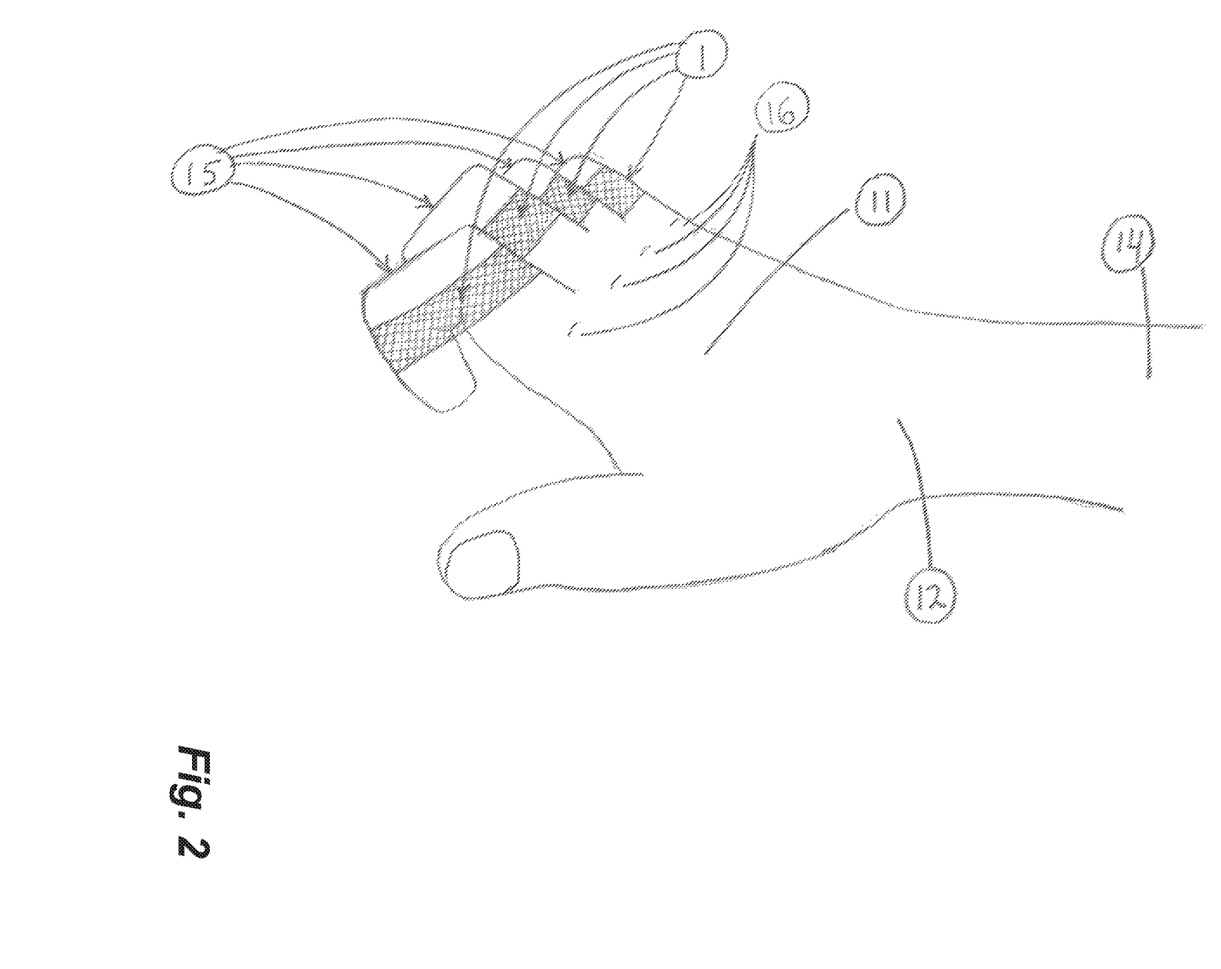
FIG. 2 is a side elevation view of an embodiment of finger straps that can be used to hold a user's fingers in a flexed position.

Referring to FIGS. 1 and 2, in some embodiments, apparatus 6 can comprise adjustable finger straps 1 which can hold the interphalangeal joints 15 of the fingers of a user's hand 11 in flexed positions, adjustable distal stabilizing strap 3 to secure apparatus 6 to a user's wrist 12, adjustable proximal stabilizing strap 4 to secure apparatus 6 to a user's upper arm 10, rigid member 5 to separate distal stabilizing strap 3 from proximal stabilizing strap 4 and keep a user's elbow 13 straight, and a winding strap 2. In combination with other elements, winding strap 2 can cause a user's wrist 12 and metacarpal phalangeal joints 16 to flex as it is pulled in a palmar direction, a user's forearm 14 to pronate, and the user's elbow 13 to be held in extension.

In some embodiments, adjustable finger straps 1 can be adjusted (loosened or tightened) to account for varying digit size by hook-and-loop fasteners (or appropriate alternatives) attached to the outside of finger straps 1. In some embodiments, these finger straps 1 can be directly attached to, or can be separate from, winding strap 2 that pulls the wrist into flexion.

Winding strap 2 can be connected, for example by sewing the straps together, to the dorsal aspect of distal stabilizing strap 3 at winding strap/distal stabilizing strap interface 21. In some embodiments, winding strap 2 can be an integral piece of material with distal stabilizing strap 3. Winding strap 2 can run over a user's hand 11 (the dorsum of a user's wrist and over the user's flexed digits), covering interphalangeal joints 15 and finger straps 1. Winding strap 2 can then run laterally (ulnarly) around the outside of the user's forearm, and be used to pull a user's interphalangeal joints 15 and wrist 12 into flexion. Winding strap 2 can further attach to distal stabilizing strap 3 at point of contact 22, wrapping around a user's forearm 14 and elbow 13 before attaching to proximal stabilizing strap 4 at point of contact 23. Fastening means such as hook-and-loop fastening material affixed to the surface of the straps can be used at points of contact 22 and 23, although it would be appreciated by those skilled in the art that other similar means of attachment could be used.

In some embodiments, distal stabilizing strap 3 can comprise a sleeve 26 (for example, a cloth sleeve) which the patient first puts their affected arm through to help hold apparatus 6 on the wrist 12 when securing distal stabilizing strap 3 to the arm. Sleeve 26 can encompass the entire arm and can also be attached to proximal stabilizing strap 4. Distal stabilizing strap 3 can act as an anchor to secure winding strap 2 and to attach to the rigid member 5.

Rigid member 5 can attach to distal stabilizing strap 3 at rigid member attachment point 24 and to proximal stabilizing strap 4 at rigid member attachment point 25. In some embodiments, proximal stabilizing strap 4 can comprise a slot on its outside surface so that the rigid member 5 can slide into it. The distance between the distal 3 and proximal stabilizing straps 4 along the rigid member 5 can be adjusted to accommodate varying user arm lengths. For example, in some embodiments, the proximal stabilizing strap 4 can slide up or down along rigid member 5 so that apparatus 6 can be adjusted to varying arm lengths.

Figure 3:
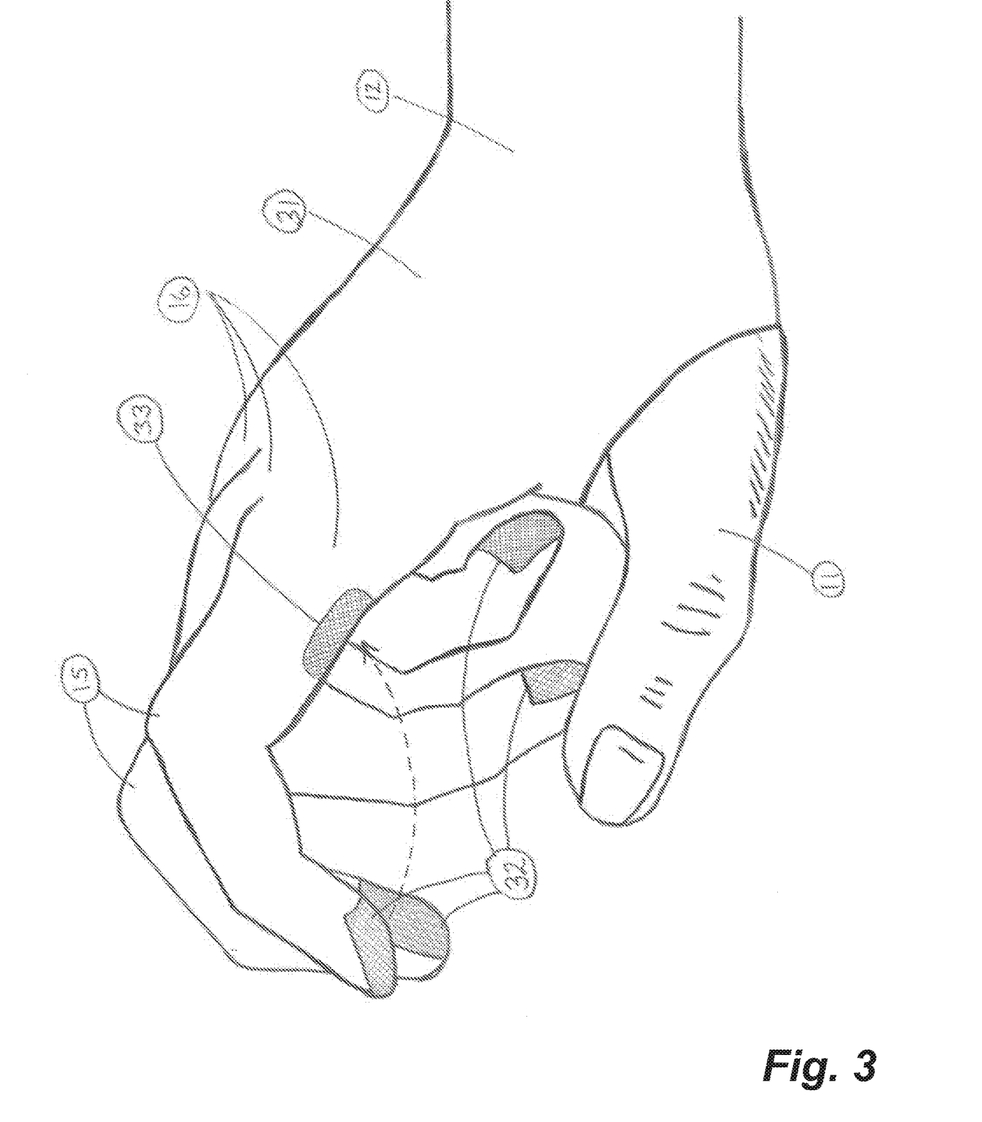
FIG. 3 is a side elevation view of an embodiment of a glove that can be used to hold a user's fingers in a flexed position.

Referring to FIG. 3, in some embodiments, glove 31 can be used as an alternative to finger straps 1 for holding a user's interphalangeal joints 15 in a flexed position. Glove 31 can comprise distal finger attachment points 32 at the tips of the glove fingers and proximal finger attachment points 33 at the base of the glove fingers. Distal finger attachment points 32 can attach to proximal finger attachment points 33 to hold a user's interphalangeal joints 15 in the desired flexed position. Fastening means such as hook-and-loop fastening material may be used at distal finger attachment points 32 and proximal finger attachment points 33 and also to adjust the fit of the glove to the user's hand, although it would be appreciated by those skilled in the art that other similar means of attachment could be used.

Referring to FIGS. 1 to 3, in operation, a user can use finger straps 1 or glove 31 to hold interphalangeal joints 15 in a flexed position, while winding strap 2 can hold wrist 12 and metacarpal phalangeal joints 16 in flexion with the forearm 14 in pronation, and winding strap 2 together with rigid member 5 can hold elbow 13 in extension. The combined effect of these positions can allow for the EDC, ECRB, and/or the supinator muscle to be stretched to a desired lengthened position.

In some embodiments, the apparatus and method can provide for a gentle prolonged stretch of these three muscles. A user can use the apparatus or method while watching TV or during other sedentary activities. It is possible for a user to use the apparatus or method while sleeping. In some embodiments, the apparatus or method can be used over the course of multiple treatments intermittently for a period of months until the user's lateral epicondylitis symptoms have subsided. The longer the duration of the treatment, the sooner the muscles will be elongated. The applied pressure, however, should not be to the extent that the tissue being stretched is irritated.

In some embodiments, apparatus 6 and methods can position the forearm extensor muscle group, specifically the muscles that originate from the lateral epicondyle, in a lengthened position to allow the muscles to stretch over time. Apparatus 6 can place the interphalangeal joints 15 of the second, third, fourth, and fifth digits (index to ring finger) into flexion, the metacarpal phalangeal joints 16 of the same digits into flexion, wrist 12 into flexion, forearm 14 into pronation and the elbow 13 into extension. The combination of these positions/movements, sustained for a period of time, can cause the muscles that attach to the lateral epicondyle to become elongated. In some cases of tennis elbow, the extensor digitorum muscle can be the muscle with the greatest restriction. The stretching of these tissues is expected to result in the reduction in the tennis elbow symptoms.

Figure 6:
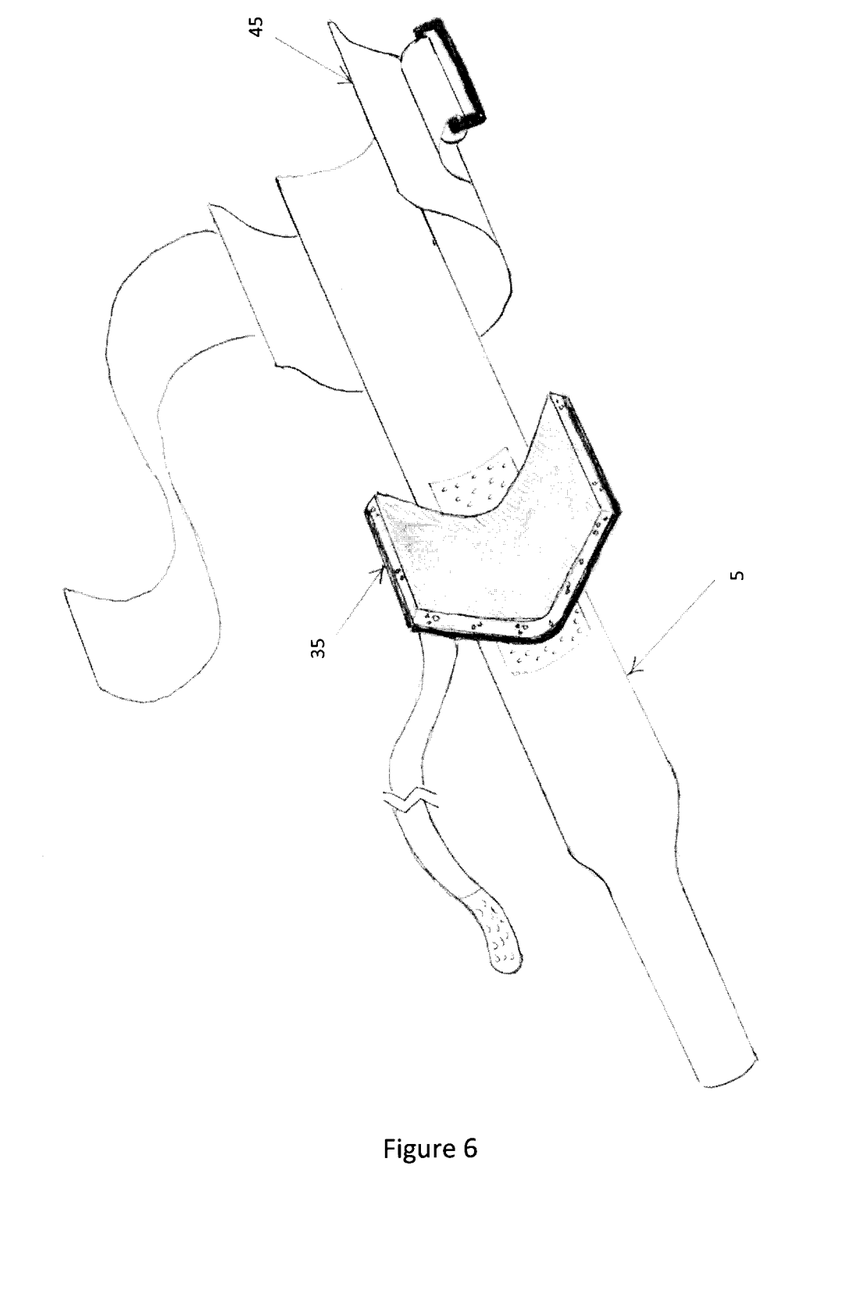
FIG. 6 is a perspective view of an embodiment of an apparatus that can be used on a user's affected arm.

In some embodiments, apparatus 6 and methods can employ a specialized glove 31, a sleeve 26, a rigid member 5, a V-shaped elbow support 35 and various straps to maintain the multiple joint positions.

Figure 4:
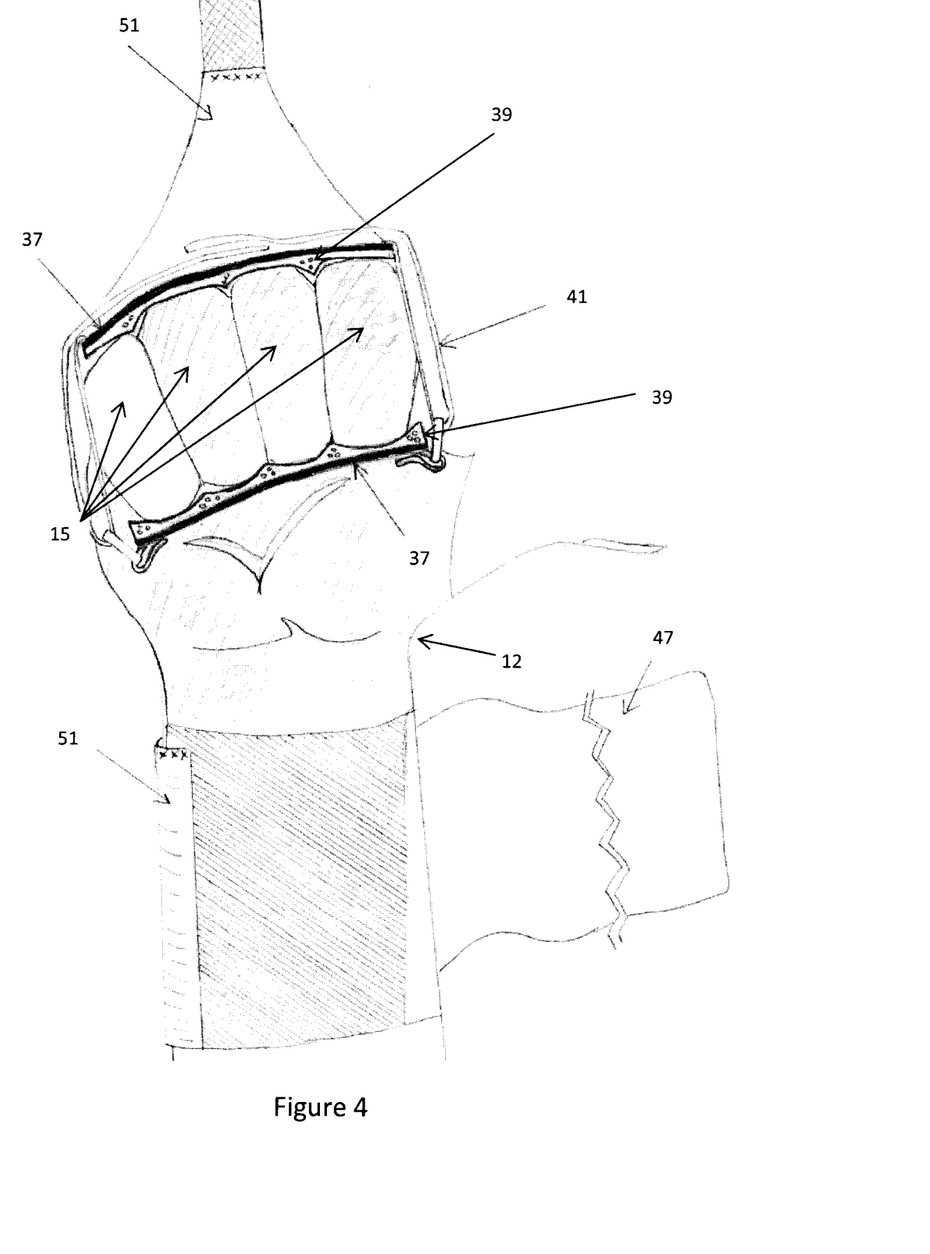
FIG. 4 is a bottom plan view of a further embodiment of a glove that can be used to hold a user's fingers in a flexed position.
Figure 5:
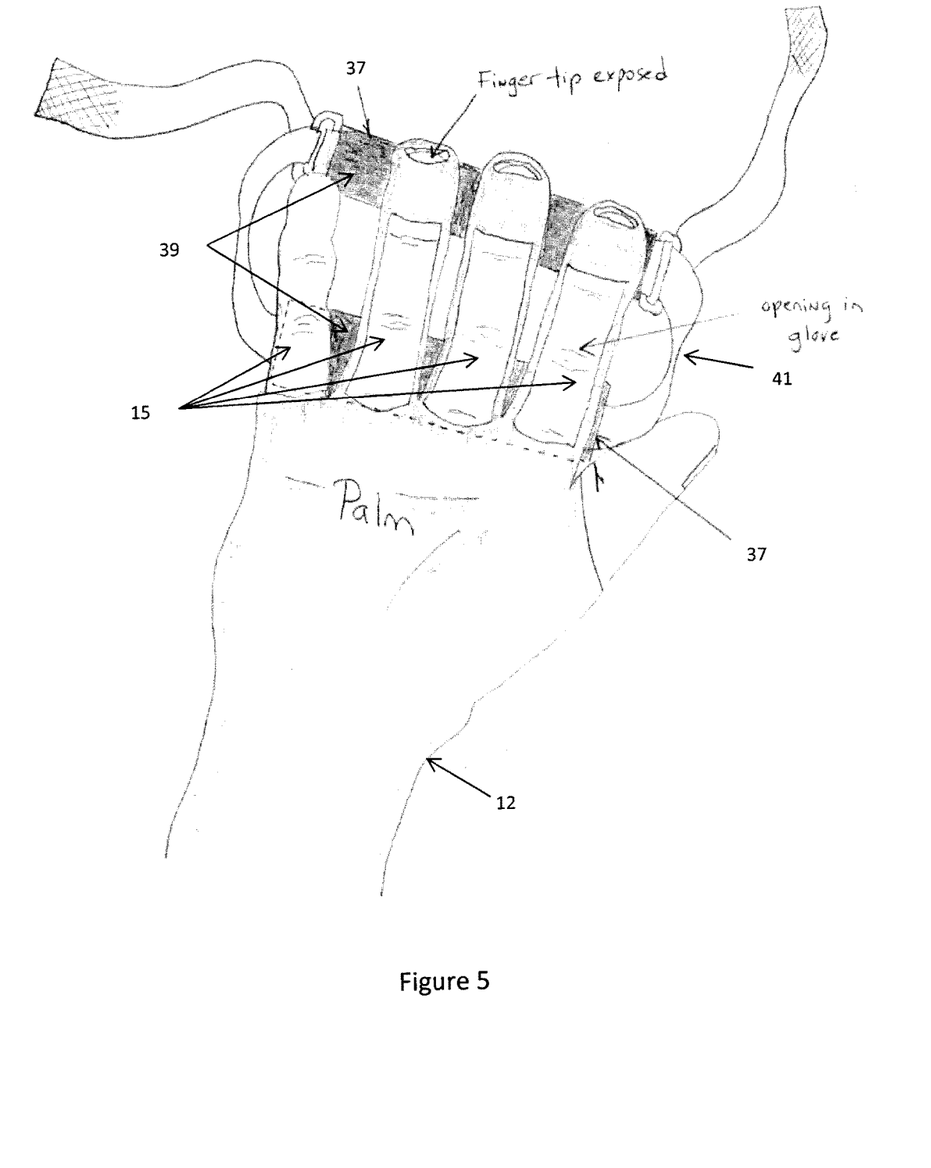
FIG. 5 is a bottom plan view of the embodiment of the glove as depicted in FIG. 4, here depicted with a user's fingers in an open position.

Referring to FIGS. 4 and 5, glove 31 can utilizes two flat bars 37 with attached cushions 39 to squeeze the interphalangeal joints 15 of the second, third, fourth, and fifth digits (index to little finger) into flexion (FIG. 4). To attain finger flexion, the patient can use their opposite (free) hand to squeeze the bars together and then secure the position with wrap-around glove straps 41, fastened by a fastening means, for example Velcro™.

Glove 31 can used to direct the fingers into a desired position. The tips of glove 31 at the second, third, and fourth digits (D2, D3, and D4) can be open at the tip to ensure that the fingers are far enough into the glove to assist with desired positioning (FIG. 5).

The rigid bars 37 can cover the proximal and distal phalanges separately. The two bars 37 used to squeeze the fingers together can be glued to the dorsal aspect of the distal phalanx and proximal phalanx portions of glove 31 respectively. The proximal bar is secured to the dorsal aspect of the glove at the perspective proximal phalanx level to D2, D3, D4 and D5. The distal bar 37 can be attached to D2, D3 and D4 of glove 31 at the distal phalanx level. In some embodiments, the fifth digit (D5) of glove 31 can have no distal finger sleeve and is therefore not attached to distal bar 37. As the fifth digit is quite a bit shorter than the other digits, generally the user actively flexes the fifth digit in unison with the other digits. The fifth digit can become held into flexion with the other digits by bars 37. The palmar aspect of the fingers can be exposed by openings 43 in glove 31, as glove 31 may restrict interphalangeal flexion.

When the fingers are flexed, strap 41 can pull the bars 37 towards each other forcing end range interphalangeal joint 15 flexion of D2, D3, D4, and D5. The straps 41 can then be secured to the proximal bar 37, for example with Velcro™ although other appropriate attachment means could be used. Both bars 37, or either one of them, can have a cushioning material 39 next to the glove 31 material to assist with patient comfort. To assist with the distal phalanges being supported by the bars 37, the tips of the digits in glove 31 can have an opening so that the flesh of the finger tips can be seen. If the finger tips are well exposed, then the digits are positioned in glove 31 far enough to a desired spot.

It would be appreciated that there are many means for holding interphalangeal joints on an affected arm in flexed positions (i.e. ways to hold the digits in flexion). While a few means have been disclosed herein and shown in the accompanying Figures, it would be understood that other appropriate means could also be used to hold interphalangeal joints in flexed positions for the purposes of the apparatuses and methods herein.

Two stabilizing straps/sleeves (45 and 47 in FIGS. 6 and 7) can help secure apparatus 6 to the user's arm. One strap can encircle the wrist 12 or forearm 14 and another can encircle the upper arm 10. These two straps 45, 47 can separated along a rigid member 5 that can run dorsal to the elbow 13. Rigid member 5 can help keep the two sleeves 45, 47 separate and can also assist in keeping the elbow 13 straight. The proximal strap at the upper arm 45 can move up or down along rigid member 5 so it can be adjusted to varying arm lengths. The distal strap 47 at wrist 12 can have a sleeve/slot 49 in which a narrow portion of rigid member 5 can slide into. This can allow for adjustment for varying lengths of forearm.

Figure 7:
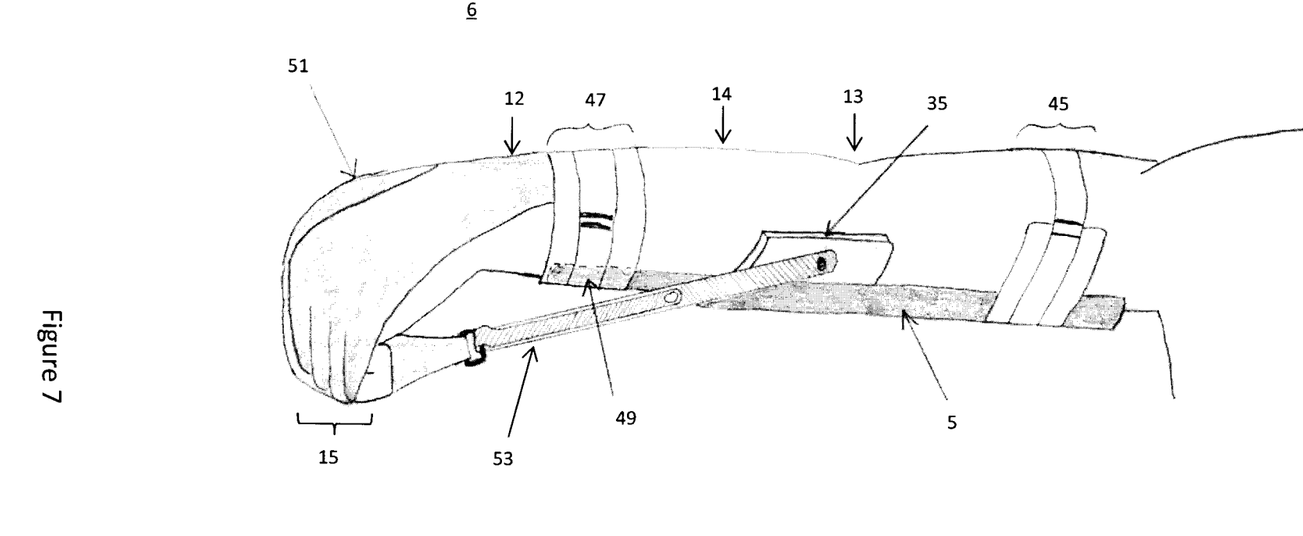
FIG. 7 is a side elevation view of an embodiment of the apparatus of FIG. 6 as used on a user's affected arm.

Distal arm sleeve/strap 47 can assist with securing the rigid member 5 against an arm snugly so that the rigid member 5 can maintain elbow 13 extension. The distal arm sleeve 47 can contain a slot 49 at the ulnar side of it in which the rigid member 5 can slide into or out of. A sleeve/slot 49 on the ulnar side of the distal sleeve 47 to receive and hold the rigid member 5 in place next to the distal forearm 14. The length of this sleeve 49 can allow the rigid member 5 to vary the depth to which it enters, allowing arms of various lengths to wear apparatus 6. This slot 49 can also allow someone to put on the glove 31 component first, followed by putting the rigid member 5 in after the glove 31 component is secure. The distal strap can also be connected to the glove 31 component. The distal arm sleeve 47 can also be the site of origin of the dorsal strap 51 which can run over the back of the hand 11.

Proximal arm sleeve/strap 45 can help hold the rigid member 5 against the arm. The proximal sleeve/strap 45 may be made of a semi rigid plastic material with Velcro™ on one of its surfaces to adhere it to the rigid arm member 5. The Velcro™ can allow it to be adjusted up or down the member 5 to allow for different arm lengths.

Rigid member 5 can be made from various possible materials. The purpose of rigid member 5 can be to maintain elbow 13 extension. In some embodiments, rigid member 5 itself can be adjustable by adjusting means in order to lengthen and shorten member 5 in response to the different arm lengths of patients.

Along rigid member 5 can also be an elbow support 35. In some embodiments, the elbow support 35 can be V-shaped to assist with the tip of the elbow 13 (the olecranon) sitting directly into the base of the V to result in a desired placement of the ulna so that the rigid member 5 can sit directly behind the elbow joint. The V-shaped elbow support can be removably secured onto the rigid stay with Velcro™ (although other appropriate fastening devices can be used) allowing it to be adjustable up and down along the rigid member 5.

A broad strap 51 can wrap over the top of the hand 11. This stretchy strap can originate securely from the distal strap 47 and can extend over the whole of the hand 11 to end distally to attach to tensioning strap 53. When broad strap 51 is pulled down and towards the lateral side of the elbow 13 from the tensioning strap 53, the wrist 12 can flex, the metacarpal phalangeal joints 16 can flex and the forearm 14 can pronate. In other words, with the interphalangeal joints 15 held in flexion, the straps 47, 51, 53 that encircle the arm can cause metacarpal phalangeal 16 flexion, wrist 12 flexion, forearm 14 pronation. The combined effect of these positions with the elbow 13 held into extension can put the tennis elbow muscles at a desired lengthened position (FIG. 7).

Strap 51 can originate from the distal strap 47, broadly covering the dorsal aspect of the hand 11. The strap 51 can be elastic, lycra-type material which can run over the back of the hand 11 and digits. This broad strap 51 can then narrow to attach to an adjustable tensioning strap 53 to finally terminate at the lateral side of elbow at support 35. The strap 51, when pulled downwards and laterally, can provide forces that can cause metacarpal flexion (D2, D3, D4, and D5), wrist 12 flexion and forearm 14 pronation.

In operation, some embodiments of apparatus 6 can be used with a relatively gentle force, holding the interphalangeal joints 15 in full flexion, the metacarpal phalangeal joints 16 in full flexion, the wrist 12 into flexion, the forearm 14 into pronation, and the elbow 13 into extension. This combination of positions, when held in position for an extended period, can cause elongation of the extensor muscle group (i.e. extensor digitorum communis, extensor carpi radialus, and the supinator muslces). In some embodiments, the stretch can be gentle and prolonged. It is possible that the patient wear apparatus 6 while watching TV or during other sedentary type of activity. After a prolonged stretch it is possible that the dorsal forearm may be uncomfortable for several minutes. The patient may also wear apparatus 6 to bed, however, after a few hours of stretching it is expected that the device will grow to be uncomfortable and may wake the individual up. The device may have to be used for several months to get the desired muscle lengthening effect. If the patient is too aggressive and applies too much force through the tensioning strap 53, the stronger stretch can potentially aggravate the condition.

It is recommended that the device be used under the guidance of a medical professional. Patients with certain conditions should be cautious when using apparatus 6 or the methods herein. Patients with compromised circulatory status to their arms, such as those with advanced diabetes, with osteoarthritis or rheumatological conditions of their wrists, hands or elbows, with unstable joints of their hand, wrist or elbow, with carpal tunnel syndrome, with acute tennis elbow (elbow pain that is less than six weeks in duration). If progressive weakness of the wrist extensors develops, use of apparatus 6 and methods should be discontinued. Sustained pronation with an extended elbow may irritate the motor branch of the radial nerve (posterior interosseous nerve) at the radial tunnel if the radial tunnel is fibrotic and restrictive.

The apparatuses and methods herein, when used as prescribed, can place the extensor digitorum communis muscle, along with extensor carpi radialis brevis and supinator muscles in their elongated/stretched postions. With the gentle prolonged muscle stretch created by the apparatuses and methods herein, the taut muscle can become stretched (elongated) over several treatments thusly normalizing the biomechanics at the wrist 12 and elbow 13. The apparatuses and methods herein can be for individuals with tennis elbow whom their medical practitioner deems to have a taught extensor or supinator muscle group. The apparatuses and methods herein can be used for prolonged periods daily. Research has shown that the elongation effect of a muscle is dependent on the total time at the end range of the muscle. The apparatuses and methods herein can be used several times throughout the day for varying lengths of time. It is recommended that the patient use a hot pack on their dorsal forearm while using the apparatuses and methods herein. Research has shown that heat promotes the elongation of the muscle being stretched. These apparatuses and methods do not have to be the only treatment for the patient. The patient may use other forms of treatment (anti-inflammatory medicine, physiotherapy, acupuncture, massage etc.) while using these apparatuses and methods at home.

In some embodiments, the use the apparatus or method can be performed in combination with other types of therapy for lateral epicondylitis, for example, the use of a hot pack, anti-inflammatory medicine, physiotherapy, acupuncture, massage, etc.)

Although particular embodiments have been shown and described, it will be appreciated by those skilled in the art that various changes and modifications might be made without departing from the scope of the invention. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

I claim:

1. An apparatus for mitigating lateral epicondylitis by stretching one or more muscles on an affected arm, the apparatus comprising:
    an article including at least one of a finger strap and a finger sleeve for holding at least one interphalangeal joint of at least one digit of the affected arm's hand in a flexed position;
    a distal stabilizing strap for securing the apparatus to a wrist portion of the affected arm;
    a proximal stabilizing strap for securing the apparatus to an upper arm portion of the affected arm;
    a rigid member separating the distal stabilizing strap from the proximal stabilizing strap for positioning the affected arm's elbow in extension; and
    a third strap releasably attachable to the distal stabilizing strap and to at least one of the proximal stabilizing strap and the rigid member, the third strap being configured to wrap around the article while the article holds the at least one interphalangeal joint in the flexed position, and to hold:
        the affected arm's wrist, the at least one interphalangeal joint, and at least one metacarpal joint of the affected arm in flexion;

the affected arm's forearm in pronation; and
the affected arm's elbow in extension.

2. The apparatus as set forth in claim 1, wherein the article comprises a plurality of finger straps to hold the at least one interphalangeal joint of the at least one digit of the affected arm's hand in a flexed position.

3. The apparatus as set forth in claim 1, wherein the article comprises a glove including at least one finger sleeve to hold the at least one interphalangeal joint of the at least one digit of the affected arm's hand in a flexed position.

4. The apparatus as set forth in claim 3, wherein each of the at least one finger sleeve has a tip and a base, and the glove comprises:
 a distal attachment point at the tip of each of the at least one finger sleeve; and
 a proximal attachment point at the base of each of the at least one finger sleeve.

5. The apparatus as set forth in claim 3, wherein the glove comprises:
 a plurality of finger sleeves;
 two flat bars attached across the plurality of finger sleeves, the flat bars configured for squeezing the at least one interphalangeal joint into flexion when the flat bars are brought towards each other; and
 at least one wrap-around glove strap configured to hold the at least one interphalangeal joint in flexion after the flat bars are brought towards each other.

6. The apparatus as set forth in claim 1, wherein the third strap comprises a winding strap configured to wind around the affected arm.

7. The apparatus as set forth in claim 1, wherein the third strap comprises an adjustable tensioning strap configured to adjust the tension of the third strap.

8. The apparatus as set forth in claim 1, wherein the apparatus is adjustable to suit affected arms of different sizes.

9. The apparatus as set forth in claim 8, wherein the apparatus is adjustable by hook-and-loop type fastening material at attachment points.

10. The apparatus as set forth in claim 8, wherein the apparatus is adjustable by the lengthening or shortening of the rigid member.

11. A method for mitigating lateral epicondylitis by stretching one or more muscles on an affected arm, the method comprising holding:
 interphalangeal joints of digits two through five of the affected arm's hand in flexed positions;
 the affected arm's wrist in flexion;
 the affected arm's forearm in pronation; and
 the affected arm's elbow in extension,
 thereby stretching the one or more muscles.

12. The method as set forth in claim 11, wherein the holding is prolonged for a period of time.

13. The method as set forth in claim 11, wherein the method is repeated until symptoms of lateral epicondylitis subside.

14. The method as set forth in claim 11, wherein the method is performed in combination with other types of therapy for lateral epicondylitis.

15. The method as set forth in claim 11, wherein the one or more muscles are selected from the group consisting of the extensor digitorum communis, extensor carpi radialis brevis, supinator muscle, and any combination thereof.

16. The method as set forth in claim 11, wherein the holding is accomplished by an apparatus for mitigating lateral epicondylitis.

17. The method as set forth in claim 16, comprising adjusting the apparatus to suit affected arms of different sizes.

18. The method as set forth in claim 11, further comprising:
 applying an article including at least one of a finger strap and a finger sleeve to the affected arm's hand to position the interphalangeal joints into the flexed positions;
 securing a rigid member to a wrist portion of the affected arm with a distal stabilizing strap and to an upper arm portion of the affected arm with a proximal stabilizing strap to position the affected arm's elbow into extension; and
 securing a wrapping strap around the article, the wrapping strap attaching the distal stabilizing strap and to at least one of the proximal stabilizing strap and the rigid member, to position the affected arm's wrist into flexion and the affected arm's forearm into pronation.

19. An apparatus for mitigating lateral epicondylitis by stretching one or more muscles on an affected arm, the apparatus comprising:
 a glove for holding interphalangeal joints of the affected arm's hand in flexed positions, the glove comprising two flat bars attached across finger sleeves of the glove, the flat bars configured for squeezing the interphalangeal joints into flexion when the flat bars are brought towards each other; and
 wrap-around glove straps configured to hold the interphalangeal joints in flexion after the flat bars are brought towards each other and while the affected arm's wrist is positioned into flexion, the affected arm's forearm is positioned into pronation, and the affected arm's elbow is positioned into extension.

20. The apparatus as set forth in claim 19, further comprising:
 a distal stabilizing strap for securing the apparatus to a wrist portion of the affected arm;
 a proximal stabilizing strap for securing the apparatus to an upper arm portion of the affected arm;
 a rigid member separating the distal stabilizing strap from the proximal stabilizing strap for positioning the affected arm's elbow in extension; and
 a wrapping strap releasably attachable to the distal stabilizing strap and to at least one of the proximal stabilizing strap and the rigid member, the wrapping strap being configured to wrap around the article while the article holds the interphalangeal joints in flexion, and to hold the affected arm's wrist in flexion, the affected arm's forearm in pronation, and the affected arm's elbow in extension.

* * * * *